United States Patent [19]

Bright

[11] Patent Number: 4,526,889
[45] Date of Patent: Jul. 2, 1985

[54] EPIMERIC AZAHOMOERYTHROMYCIN A DERIVATIVE, INTERMEDIATES AND METHOD OF USE

[75] Inventor: Gene M. Bright, Groton, Conn.

[73] Assignee: Pfizer Inc., New York, N.Y.

[21] Appl. No.: 601,185

[22] Filed: Apr. 17, 1984

Related U.S. Application Data

[63] Continuation-in-part of Ser. No. 441,979, Nov. 15, 1982, abandoned.

[51] Int. Cl.$^3$ .................... A61K 31/71; C07H 17/08
[52] U.S. Cl. ................................... 514/29; 536/7.2; 536/7.4
[58] Field of Search ............... 536/7.2, 7.4; 424/180; 514/29

[56] References Cited

U.S. PATENT DOCUMENTS

| | | | |
|---|---|---|---|
| 3,478,014 | 11/1969 | Djokic et al. | 260/210 |
| 3,574,185 | 4/1971 | Tamburasev et al. | 536/7.4 |
| 3,660,376 | 5/1972 | Massey | 536/7.4 |
| 3,674,773 | 7/1972 | Kurath | 536/7.2 |
| 3,681,326 | 8/1972 | Von Esch | 536/7.4 |
| 4,316,010 | 2/1982 | Nagel | 536/7.2 |
| 4,328,334 | 5/1982 | Kobrehel et al. | 536/7.4 |
| 4,349,545 | 9/1982 | d'Ambrieres et al. | 536/7.4 |
| 4,382,085 | 5/1983 | Sciavolino et al. | 536/7.2 |

FOREIGN PATENT DOCUMENTS

2094293 9/1982 United Kingdom .

OTHER PUBLICATIONS

BNA's "Patent, Trademark & Copyright Journal", vol. 29, 11/84.
Lullmann et al., "CRC Critical Reviews in Toxicology", 11/75, pp. 185-218.
Massey et al., Tetrahedron Letters, pp. 157-160, 1970.

*Primary Examiner*—Johnnie R. Brown
*Attorney, Agent, or Firm*—Charles J. Knuth; Albert E. Frost; Robert K. Blackwood

[57] ABSTRACT

Antibacterial 4"-epi-9-deoxo-9a-methyl-9a-aza-9a-homoerythromycin A, pharmaceutically-acceptable salts thereof, pharmaceutical compositions comprising antibacterially-effective amounts thereof, a method of treatment of bacterial infections with antibacterially effective amounts thereof, and intermediates for the synthesis thereof from erythromycin A.

18 Claims, No Drawings

EPIMERIC AZAHOMOERYTHROMYCIN A DERIVATIVE, INTERMEDIATES AND METHOD OF USE

CROSS REFERENCE TO RELATED APPLICATION

This application is a continuation-in-part of co-pending application, Ser. No. 441,979, filed Nov. 15, 1982, now abandoned.

BACKGROUND OF THE INVENTION

The present invention is concerned with antibacterial 4''-epi-9-deoxo-9a-methyl-9a-aza-9a-homoerythromycin A, pharmaceutically-acceptable salts thereof, and intermediates useful in the preparation thereof from erythromycin A.

Erythromycin A is a well-known macrolide antibiotic, having the formula (I), which has found extensive clinical use.

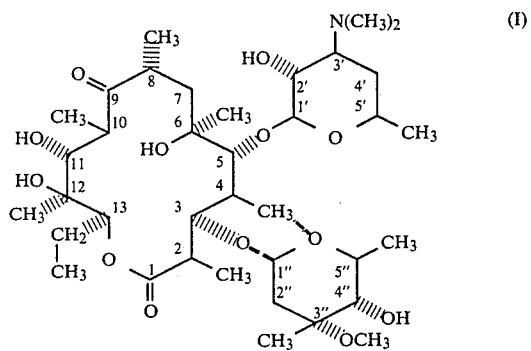

The present therapeutic compound is the 4''-epimer of the previously reported erythromycin A derivative of the formula (II), the

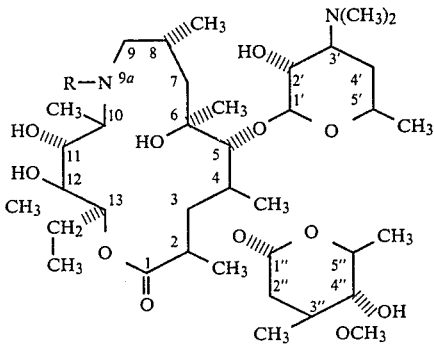

(II) R=methyl
(III) R=hydrogen subject of Belgian Pat. No. 892,357, as well as of my co-pending U.S. application, Ser. No. 399,401, filed July 19, 1982, now abandoned. In that Belgian patent, the compound of the formula (II) is named as the N-methyl derivative of "11-aza-10-deoxo-10-dihydroerythromycin A", a name coined earlier by Kobrehel et al., U.S. Pat. No. 4,328,334 for the precursor compound of the formula (III). For the latter ring expanded (homo), aza (nitrogen substituted for carbon) erythromycin A derivative, we prefer the name 9-deoxo-9a-aza-9a-homoerythromycin A. That compound could also be named as a 10-aza-14-hexadecanolide derivative.

Certain of the present novel intermediates are likewise 4''-epimers of previously known compounds. Thus 4''-epi-9-deoxo-9a-aza-9a-homoerythromycin A is the 4''-epimer of the above compound of the formula (III); and 4''-epi-erythromycin A oxime is the 4''-epimer of the erythromycin A oxime of Djokic et al., U.S. Pat. No. 3,478,014. 4''-Epi-erythromycin A is the subject of co-pending U.S. patent application, Ser. No. 353,547, filed Mar. 1, 1982 by Sciavolino et al, now U.S. Pat. No. 4,382,085.

SUMMARY OF THE INVENTION

The present invention encompasses the antibacterial compound 4''-epi-9-deoxo-9a-methyl-9a-aza-9a-homoerythromycin A, having the formula (IV), pharmaceutically-acceptable salts thereof, pharmaceutical compositions thereof, and a method of use thereof in the treatment of bacterial infections in mammals.

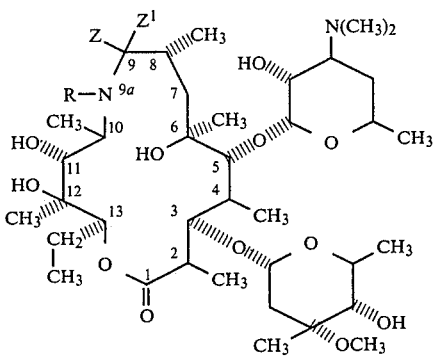

(IV) R=methyl, Z=Z$^1$=hydrogen
(V) R=hydrogen, Z and Z$^1$ together=oxygen
(VI) R=Z=Z$^1$=hydrogen The present therapeutic compound (IV) shows a relatively broad spectrum of antibacterial activity which includes erythromycin A susceptible organisms and, in addition, fully incorporates the major respiratory pathogen *Hemophilus influenzae*. Its high oral absorption and extraordinarily long half-life *in vivo* renders compound (IV) of especial value in the oral treatment of susceptible bacterial infections in mammals.

The present invention also encompasses intermediates useful in the synthesis of 4''-epi-9-deoxo-9a-methyl-9a-aza-9a-homoerythromycin A (IV) as follows:

(a) A compound selected from the group consisting of 4''-epi-9a-aza-9a-homoerythromycin A and the 9-deoxo derivative thereof, of the above formulae (V) and (VI), respectively.

(b) 4''-Epi-erythromycin A oxime.

(c) A compound selected from the group consisting of 9a-benzyloxycarbonyl-9-deoxo-4''-deoxy-4''-oxo-9a-aza-9a-homoerythromycin A, of the formula (VII); 9-deoxo-4''-deoxy-4''-oxo-9a-methyl-9a-aza-9a-homoerythromycin A, of the formula (VIIa); and the corresponding 2'-O-(C$_2$-C$_3$)alkanoyl derivatives thereof of the formulae (VIII) and (VIIIa). Acetyl is the preferred value of 2'-O-(C$_2$-C$_3$)alkanoyl.

3

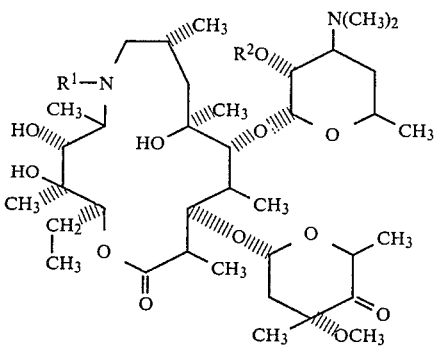

(VII) $R^1$=benzyloxycarbonyl, $R_2$=H (VIII) $R^1$=benzyloxycarbonyl, $R^2$=($C_2$-$C_3$)alkanoyl (VIIa) $R^1$=methyl, $R^2$=H (VIIIa) $R^1$=methyl, $R^2$=($C_2$-$C_3$)alkanoyl (d) A compound selected from the group consisting of the 2'-O-acetyl- and the 2'-O-propionyl-9-deoxo-9a-benzoyloxycarbonyl-9a-aza-9a-homoerythromycin A, of the formula (IX). The 2'-O-acetyl derivative is of particular value.

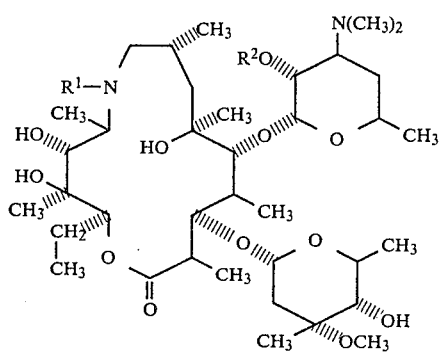

(IX) $R^1$=benzyloxycarbonyl, $R^2$=($C_2$-$C_3$)alkanoyl and (e) A compound selected from the group consisting of 4''-epi-9-deoxo-9a-hydroxy-9a-aza-9a-homoerythromycin A 3'-N-oxide and 4''-epi-9-deoxo-9a-methyl-9a-aza-9a-homoerythromycin A 3'-N-oxide, of the formulae (X) and (XI), respectively.

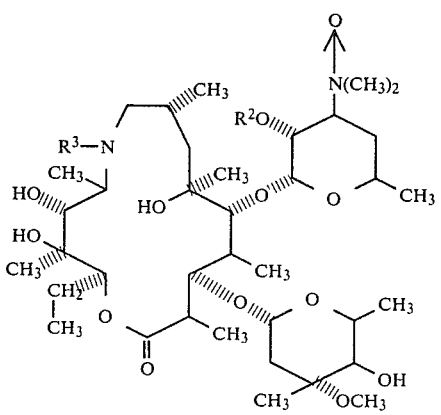

(X) $R^3$=hydroxy
(XI) $R^3$=methyl

4

DETAILED DESCRIPTION OF THE INVENTION

The antibacterial compound of the present invention, 4''-epi-9-deoxo-9a-methyl-9a-aza-9a-homoerythromycin A (IV), is readily prepared by a number of routes from erythromycin A. These routes, which variously proceed via novel and known compounds as intermediates, involve intrinsic transformations as follows:

(A) C-4'' epimerization;
(B) ring expansion, with introduction of 9a-nitrogen;
(C) removal of the 9-oxo group; and
(D) 9a-N-methylation;

together with any optional or necessary introduction and removal of protecting groups. Preferred are one or the other of the following sequences of transformations: (A)(B)(C)(D), (B)(A)(C)(D) or (B)(C)(D)(A). The various intermediates and final product are isolated by standard manipulative methods (e.g., extraction, precipitation, evaporation, chromatography, crystallization).

(A)(B)(C)(D)

The operational sequence (A)(B)(C)(D) involves initial conversion of erythromycin A (I) to 4-epi-erythromycin A, according to the method of Sciavolino et al. (supra). The latter is then converted, in virtually quantitative yield, to 4''-epi-erythromycin A oxime by reaction with hydroxylamine or preferably, a hydroxylamine salt such as the hydrochloride. Under presently discovered, preferred conditions, at least one molar equivalent, usually an excess, e.g., 10–30 equivalents, of the hydroxylamine is employed; in an excess of a weakly basic, tertiary amine (preferably pyridine) as solvent; at a temperature in the range 0°–50°, conveniently at ambient temperature.

The resulting 4''-epi-erythromycin oxime is rearranged to the 4''-epi-9a-aza-9a-homo derivative (V) via a Beckman rearrangement. The preferred conditions employ an excess (e.g., 3–4 molar equivalents) of an organic sulfonyl chloride, preferably methane sulfonyl chloride, which is reacted with the oxime (as free base or as an acid salt) in a mixture of a lower ketone (e.g., methyl ethyl ketone, acetone) and water containing a large molar excess of sodium bicarbonate, at a temperature of 0°–50° C., preferably at 0°–30° C.

The C-9 amide carbonyl of (V) is then conveniently reduced to the corresponding dihydro derivative, i.e., 4''-epi-9-deoxo-9a-aza-9a-homoerythromycin A (VI) by reduction with sodium borohydride (preferably in excess to force the reaction to completion in a reasonable time period, but with at least two equivalents). The reduction is carried out in a suitable protic solvent, such as a lower alkanol (preferably methanol) at 0°–50° (preferably at or below 38°). Excess $NaBH_4$ is carefully decomposed by quenching the reaction in dilute aqueous acid.

Final methylation to yield the compound (IV) is accomplished by reductive methylation, using formaldehyde in the presence of a reducing agent, such as hydrogen and a noble metal catalyst, sodium cyanoborhydride, or, preferably, formic acid. The reaction is preferably carried out with at least one equivalent each of formaldehyde and formic acid in a reaction inert solvent at 20°–100° C. The preferred solvent is chloroform. In this solvent, reactants are conveniently combined at ambient temperature and then heated at reflux to force the reaction to completion Alternatively, methylation of (VI) to (IV) is accomplished by oxidatively protecting the dimethylamino group as its N-oxide (simultaneously forming the 9a-N-hydroxy derivative), methylating with methyl iodide, with (at least in part) simultaneous 9a-N-deoxygenation, and reduction of the resulting 9a-methyl-3''-N-oxide Oxidation of (VI) is readily accomplished by reaction with hydrogen peroxide, generally in excess of the minimum necessary two molar equivalents, in a reaction inert solvent at 10°–50° C., conveniently at ambient temperature. In this manner 9a-hydroxy-3'-N-oxide (X) is formed. The latter is methylated and deoxygenated to (XI) with methyl iodide conveniently in a reaction inert solvent (e.g., methylene chloride) at 0°–50° C. (conveniently at ambient temperature), preferably in the presence of a solvent insoluble base which will neutralize formed acid (e.g., HI when methyl iodide is the methylating agent). With methylene chloride as solvent, an excess of potassium carbonate is the base of choice. Thus the excess base and formed sodium iodide are completely removed by simple filtration prior to isolation of the 9a-methyl-3'-N-oxide (XI). Finally, removal of the 3'-N-oxide group is readily accomplished by hydrogenation over a noble metal or Raney nickel catalyst. In this hydrogenation, temperature and pressure are not critical, e.g., suitably 0°–100° C. and a pressure which ranges from subatmospheric to 100 atmospheres or more. Most convenient are ambient temperature and moderate pressures, e.g., 2–8 atmospheres. Suitable noble metal catalysts include palladium rhodium and platinum, of the supported or non-supported type, well known in the art of catalytic hydrogenation. The preferred catalysts are palladium supported on carbon and Raney nickel.

(B)(A)(C)(D)

The operational sequence (B)(A)(C)(D) involves initial conversion of erythromydin A (I) to 9-deoxo-9a-aza-9a-homoerythromycin (III), via erythromycin A oxime and 9a-aza-9a-homoerythromycin, according to the method of Kobrehel et al (supra). In this connection, the novel process, described above for 4''-epi-erythromycin A oxime, is advantageously employed for the preparation of the intermediate erythromycin A oxime.

The 2'-hydroxy group of compound (III) is first protected in the form of its acetate or propionate ester. Acylation is selectively accomplished by reacting compound (III) with a limited excess of acetic or propionic anhydride in a reaction inert solvent (e.g., methylene chloride) at 0°–30° C. (conveniently ambient temperature). The limited excess of anhydride is used to compensate for reagent consumed in side reactions, e.g., undesired acylation of other groups, particularly the 9a-nitrogen.

The resulting 2'-($C_2$-$C_3$)alkanoyl derivative is then protected on 9a-nitrogen with a benzyloxycarbonyl group. Thus compound (IX) is formed by reaction of the above 2'-ester with carbobenzoxy chloride, in a reaction inert solvent in the presence of a base. Particularly well suited are Schotten-Baumann conditions, i.e., reaction of the 2'-ester with the acid chloride under aqueous, alkaline conditions, e.g., aqueous tetrahydrofuran, maintaining the pH 7.5–8.5 with dilute NaOH as the acid chloride is added and as the reaction proceeds. Temperature is not critical, but will generally be in the range 0°–50° C., conveniently ambient.

The C-4'' hydroxyl compound (IX) is then oxidized to C-4''-oxo compound (VIII) by the action of oxalyl chloride/dimethylsulfoxide at low temperature (−40° to −80° C.) in a reaction inert solvent (e.g., methylene chloride), followed by treatment of the cold reaction mixture with an excess of a tertiary amine (e.g., triethylamine). The alkanoate ester protecting group is removed by solvolysis, preferably by contact with excess methanol at 0°–100° C. thereby forming compound (VII).

Hydrogenation over Raney nickel catalyst, using conditions as described above, converts compound (VII) to 4''-epi-9-deoxo-9a-aza-9a-homoerythromycin A (VI). The latter is converted to the 9a-N-methyl derivative (IV) according to one of alternative methods as described above.

(B)(C)(D)(A)

This operational sequence involves initial conversion of erythromycin A to the above compound of the formula (II) according to my above cited co-pending application, using methods detailed in the Preparation section below. C-4'' epimerization is then accomplished according to the steps and methods described above. The 2'-hydroxy group is protected by acylation, the 4''-hydroxy group is oxidized to the 4''-oxo group, preferably substituting trifluoroacetic anhydride for oxalyl chloride; the protecting acyl group is removed; and the 4''-oxo group catalytically hydrogenated to the desired 4''-epimeric hydroxy group. In this case, the preferred catalyst is Raney nickel.

Since compound (IV) of the present invention contains two basic nitrogen atoms, pharmaceutically acceptable mono and di acid addition salts are formed by contacting the free base (IV), respectively, with substantially one equivalent of the acid or with at least two equivalents of the acid. Salts are generally formed by combining the reagents in a reaction inert solvent; if the salt does not precipitate directly, it is isolated by concentration and/or addition of a nonsolvent. Suitable pharmaceutically acceptable acid addition salts include, but are not restricted to those with HCl, HBr, $HNO_3$, $H_2SO_4$, $HO_2CCH_2CH_2CO_2H$, cis- and trans- $HO_2CCHCHCO_2H$, $CH_3SO_3H$ and p-$CH_3C_6H_4SO_3H$.

The antibacterial activity of the compound of the formula (IV) is demonstrated by measuring its minimum inhibitory concentrations (MIC's) in mcg./ml. against a variety of microorganisms in brain heart infusion (BHI) broth. Generally twelve 2 fold dilutions of the test compound are employed, with initial concentration of the test drug being in the range of 50 to 200 mcg./ml. The susceptibility (MIC) of the test organism is accepted as the lowest concentration of compound capable of producing complete inhibition of growth as judged by the naked eye. A comparison of the activity of 4''-epi-9-deoxo-9a-methyl-9a-aza-9a-homoerythromycin A (IV) with that of an erythromycin A control is shown in replicate in the Table I.

TABLE I

| In vitro Activity of Compound (IV) | | | | | |
|---|---|---|---|---|---|
| | | Replicate MIC Values | | | |
| | | Day 1 | | Day 2 | |
| | | A | B | A | B |
| Staph. aur. | 005 | 0.05 | 0.20 | 0.05 | 0.39 |
| | 052 | 0.10 | 0.20 | 0.10 | 0.39 |
| | 400 | 3.12 | 3.12 | 6.25 | 12.5 |
| Staph. epi | 111 | 0.05 | 0.10 | 0.05 | 0.20 |
| Strep. faec. | 006 | 0.78 | 1.56 | 0.78 | 0.78 |
| Strep. pyog. | 203 | 0.025 | 0.025 | 0.025 | 0.025 |
| Strep. pneumo. | 012 | 0.025 | 0.025 | 0.025 | 0.025 |

TABLE I-continued

In vitro Activity of Compound (IV)

| | | Replicate MIC Values | | | |
|---|---|---|---|---|---|
| | | Day 1 | | Day 2 | |
| | | A | B | A | B |
| E. Coli | 125 | (a) | 6.25 | (a) | 6.25 |
| | 129 | (a) | 1.56 | (a) | 6.25 |
| | 266 | (a) | 3.12 | (a) | 6.25 |
| | 470 | 3.12 | 0.78 | 3.12 | 0.78 |
| Kleb. pn. | 009 | (a) | 12.5 | (a) | 12.5 |
| | 031 | (a) | 12.5 | (a) | 12.5 |
| Kleb. oxy. | 024 | (a) | 12.5 | (a) | 12.5 |
| Past. mult. | 001 | 1.56 | 0.10 | 1.56 | 0.10 |
| Serr. mar. | 017 | (a) | 50 | (a) | 50 |
| Neiss. sic. | 000 | 1.56 | 0.20 | 3.12 | 0.39 |
| Ent. aerog. | 040 | (a) | 12.5 | (a) | 12.5 |
| Ent. cloac. | 009 | (a) | 25 | (a) | 25 |
| Prov. strua. | 013 | (a) | 50 | (a) | 50 |
| H. influ. | 012 | 3.12 | 0.39 | 1.56 | 0.39 |
| | 036 | 6.25 | 0.39 | 3.12 | 0.39 |
| | 038 | 6.25 | 0.39 | 3.12 | 0.78 |
| H. influ. | 042 | 1.56 | 0.39 | 1.56 | 0.39 |
| | 051 | 3.12 | 0.39 | 3.12 | 0.78 |
| | 073 | 3.12 | 0.39 | 3.12 | 0.78 |
| | 078 | 1.56 | 0.39 | 1.56 | 0.39 |
| | 081 | 3.12 | 0.39 | 3.12 | 0.78 |

(a) greater than 50
A Erythromycin A control
B Compound (IV)

Additionally, compound (IV) is tested in vivo by the well-known mouse protection test, or by a microbiological (bioassay) determination of serum levels in a variety of mammals (e.g., mouse, rat, dog). Using rats as the test species, compound (IV) has been shown to be exceptionally well absorbed after oral dosage, providing exceptionally high and long lasting serum levels.

For the treatment of systemic infections in animals, including man, caused by susceptible microorganisms, compound (IV) is dosed at a level of 2.5–100 mg./kg. per day, preferably 5–50 mg./kg./day, in divided doses, or preferably by a single daily dose. Variation in dosage will be made depending upon the individual and upon the susceptibility of the microorganism. These compounds are dosed orally or parenterally, the preferred route being oral. The susceptibility of microorganisms isolated in the clinics is routinely tested in clinical laboratories by the well-known disc-plate method. Compound (IV) is generally the compound of choice when it shows a relatively large zone of inhibition against the bacteria causing the infection to be treated Preparation of optimal dosage forms will be by methods well known in the pharmaceutical art. For oral administration, the compounds are formulated alone or in combination with pharmaceutical carriers such as inert solid diluents, aqueous solutions or various non-toxic organic solvents in such dosage forms as gelatin capsules, tablets, powders, lozenges, syrups and the like. Such carriers include water, ethanol, benzyl alcohol; glycerin, propylene glycol, vegetable oils, lactose, starches, talc, gelatins, gums and other well known carriers. The parenteral dosage forms required for the above systemic use are dissolved or suspended in a pharmaceutically-acceptable carrier such as water, saline, sesame oil and the like. Agents which improve the suspendability and dispersion qualities can also be added.

For the topical treatment of superficial infections in animals, including man, caused by susceptible microorganisms, the compound (IV) is formulated by methods well known in the pharmacist's art into lotions, ointments, creams, salves, gels, or the like at concentrations in the range 5–200 mg./cc. of the dosage form, preferably in the range 10–100 mg./cc. The dosage form is applied at the site of infection ad libitum, generally at least once a day.

The present invention is illustrated by the following examples. However, it should be understood that the invention is not limited to the specific details of these examples. Unless otherwise specified, all operations were carried out at ambient temperature; all solvent stripping was carried out in vacuo from a bath at 40° or less; all listed temperatures are in degrees Centigrade; all thin layer chromatography (tlc) was carried out on commercial silica gel plates (using the eluant indicated in parentheses); and all solvent ratios are by volume. THF is used for tetrahydrofuran, and DMSO is used for dimethylsulfoxide.

EXAMPLE 1

4''-Epi-erythromycin A Oxime [Oxime of 4''-Epimer of (I)]

4''-Epi-erythromycin A (50 g., 0.0646 mole) was dissolved in 265 ml. pyridine. Hydroxylamine hydrochloride (112.2 g., 1.615 mole) was added and the slurry stirred 16 hours. The reaction mixture was stripped to a thick slurry, diluted with 300 ml. isopropanol, stirred well and filtered with $3 \times 100$ ml. isopropanol for wash. The filtrate and washes were combined, stripped to a water-soluble foam, and triturated with ether to yield crude title product as the hydrochloride salt (100 g.). The latter was purified by distributing between $CH_2Cl_2$ aqueous $NaHCO_3$ adjusted to pH 9.5 with dilute NaOH. The aqueous layer was separated and washed with ethyl acetate and then ether. All organic layers were combined, dried ($Na_2SO_4$) and stripped to yield title product as a white foam, 59.5 g.; tlc $R_f$ 0.5 (60:10:1 $CH_2Cl_2:CH_3OH$:conc. $NH_4OH$); $^1$Hnmr ($CDCl_3$)delta 2.31 [6H, s, $(CH_3)_2N$—], 3.32 (3H, s, cladinose $CH_3O$—).

EXAMPLE 2

4''-Epi-9a-aza-9a-homoerythromycin A (V)

Title product of the preceding Example (59.2 g., 0.0787 mole) was dissolved in 400 ml. acetone. A slurry of $NaHCO_3$ (60 g.) in 225 ml. $H_2O$ was added. Methanesulfonyl chloride (36.3 g., 24.5 ml.) in 50 ml. acetone was added portionwise over 10 minutes, while maintaining the temperature less than 30° by means of a cooling bath. The mixture was stirred 4.5 hours, stripped of acetone, $CH_2Cl_2$ (400 ml.) added to the aqueous residue, and the pH adjusted to 5.6 with 6N HCl. The aqueous layer was separated, washed with two additional portions of $CH_2Cl_2$ and then adjusted to pH 9.5 with 6N NaOH. The basic solution was extracted $2 \times$ fresh $CH_2Cl_2$, $1 \times$ ethyl acetate and $1 \times$ ether. The basic organic extracts were combined, dried ($Na_2SO_4$) and stripped to yield title product as an ivory foam, 41 g.; tlc $R_f$ 0.4 (60:10:1 $CH_2Cl_2:CH_3OH$:conc. $NH_4OH$); $^1$Hnmr ($CDCl_3$)delta 2.27 [6H, s, $(CH_3)_2N$—], 3.29 (3H, s, cladinose $CH_3O$—); $^{13}$Cnmr [$CDCl_3$, $(CH_3)_4$ Si internal standard] ppm 177.24 (lactone C=O), 163.53 (amide C=O), 102.29 and 95.24 (C-3, C-5), 40.22 [$(CH_3)_2N$—].

EXAMPLE 3

2'-O-Acetyl-9-deoxo-9a-aza-9a-homoerythromycin A [2'-O-Acetate of (III)]

9-Deoxo-9a-aza-9a-homoerythromycin A (10 g., 0.0136 mole; (III); U.S. Pat. No. 4,328,334) was dissolved in 150 ml. of $CH_2Cl_2$. Acetic anhydride (1.39 g., 1.28 ml., 0.0136 mole) was added and the mixture stirred 3 hours. The acetylation was monitored by tlc; to force the reaction to completion, 0.25 ml. acetic anhydride and then 0.5 ml. acetic anhydride were added, with additional stirring for 1.5 and 1 hour respectively. The reaction mixture was diluted with $H_2O$ and the pH adjusted to 11 with dilute NaOH. The organic layer was separated, dried ($NaSO_4$), and stripped to a foam, 11.5 g. The foam (10 g.) was chromatographed on 300 g. silica gel with 9:1 $CH_2Cl_2$:$CH_3OH$ as eluant and tlc monitoring. A less polar impurity (3.6 g.) was eluted, followed by purified title product, isolated as a white foam, 2 g.; tlc Rf 0.2 (90:10:1 $CH_2Cl_2$:$CH_3OH$:conc. $Nh_4OH$); $^1Hnmr$ ($CDCl_3$)delta 2.02

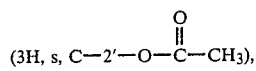

2.26 [6H, s, $(CH_3)_2N$—], 3.35 (3H, s, cladinose $CH_3OH$—).

By the same method, substituting propionic anhydride for acetic anhydride, the corresponding 2'-O-propionyl derivative is prepared.

EXAMPLE 4

2'-O-Acetyl-9-deoxo-9a-benzyloxycarbonyl-9a-aza-9a-homoerythromycin A [(IX), $R^2$=acetyl]

Title product of the preceding Example (1.7 g., 0.00219 mole) was dissolved in 70 ml. 5:2 THF:$H_2O$. The pH was adjusted to 8 with dilute NaOH. Carbobenzoxy chloride (0.51 g., 0.427 ml., 0.003 mole) was added and the mixture stirred for 2 hours with further addition of dilute NaOH as necessary to maintain pH 8. Since tlc indicated reaction incomplete, more carbobenzoxy chloride (0.3 ml.) was added, and reaction continued for 3 hours, still maintaining pH 8. The reaction was quenched with copious $H_2O$ and ethyl acetate, the pH was adjusted to 9.6, and the aqueous layer washed with $CH_2Cl_2$. The organic layers were combined, dryed ($Na_2SO_4$) and stripped to a foam, 2.4 g. The foam was chromatographed on 85 g. silica gel, eluting with 170:10:1 $CH_2Cl_2$:$CH_3OH$:conc. $NH_4OH$. Pure fractions were combined, stripped to a foam, taken up in $CH_2Cl_2$ and concentrated until title product crystallized, 1.2 g.; m.p. 122°; tlc Rf 0.4 (90:10:1 $CH_2Cl_2$:$CH_3OH$:conc. $NH_4OH$); $^1Hnmr$ ($CDCl_3$)delta 2.00

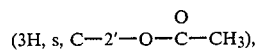

2.27 [6H, s, $(CH_3)_2N$—], 3.35 (3H, s, cladinose $CH_3O$—); $^{13}Cnmr$ [$CDCl_3$, $(CH_3)_4$ Si internal standard] ppm 176.31 (lactone C=O), 169.36 (C-2' ester C=O), 157.10 (carbamate C=O); 137.0, 127.55 and 127.92 (aromatic ring); 40.6 [$(CH_3)_2N$—].

By the same method, the 2'-O-propionyl derivative of the preceding Example is converted to the corresponding 2'-O-propionyl-9a-benzyloxycarbonyl derivative.

EXAMPLE 5

2'-O-Acetyl-9a-benzyloxycarbonyl-9-deoxo-4''-deoxy-4''-oxo-9a-aza29a-homoerythromycin A [(VIII), $R^2$=acetyl]

Oxalyl chloride (4.37 g., 3.0 ml., 0.0344 mole) was dissolved in 25 ml. $CH_2Cl_2$ and cooled to −60°. DMSO (6.70 g., 6.09 ml., 0.0856 mole) in 9 ml. $CH_2Cl_2$ was added. After holding the mixture at −60° for 10 minutes, title product of the preceding Example (5.2 g., 0.00572 mole) in 16 ml. $CH_2Cl_2$ was added at the same temperature. After a further 25 minutes at −60°, triethylamine (17.3 g., 23.9 ml., 0.172 mole) was added and the mixture warmed to room temperature, diluted with 50 ml. $H_2O$ and excess $NaHCO_3$. The organic layer was separated, dried ($Na_2SO_4$) and stripped to yield title product as a tacky foam, 6.8 g.; tlc Rf 0.6 (90:10:1 $CH_2Cl_2$:$CH_2OH$:conc. $NH_4OH$); $^1Hnmr$ ($CDCl_3$) delta 2.05

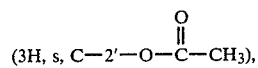

2.25 [6H, s, $(CH_3)_2N$—], 3.32 (3H, s, cladinose $CH_3O$—), 7.37 (5H, s, aromatic protons); MS: major peaks at m/e 536 and 518 [N-benzyloxycarbonyl aglycone ion (minus both sugars via cleavage at C-1'', C-5)], 200 (base peak, desosamine-derived fragment), 125 (neutral sugar-derived fragment). This intermediate is preferably used immediately in the next step.

In like manner, the corresponding 2'-O-propionyl-4''-oxo derivative is prepared from the 2'-O-propionyl compound of the preceding Example.

EXAMPLE 6

9a-Benzyloxycarbonyl-9-deoxo-4''-deoxy-4''-oxo-9a-aza-9a-homoerythromycin A (VII)

Title product of the preceding Example, 1.0 g. was stirred in 25 ml. methanol for 65 hours, then stripped to a foam. The foam was taken up in $CH_2Cl_2$, washed with saturated $NaHCO_3$, and restripped to a second foam. The second foam was chromatographed on 20 g. silica gel using 13:1 $CH_2Cl_2$:$CH_3OH$ as eluant. Clean product fractions were combined and stripped to yield purified title product as a foam, 336 mg.; tlc Rf 0.4 (90:10:1 $CH_2Cl_2$:$CH_3OH$:conc. $NH_4OH$; $^{13}Cnmr$ [$CDCl_3$, $(CH_3)_4$ Si internal standard] ppm 210.87 (C-4 C=O), 176.03 (lactone C=O), 157.41 (carbamate C=O); 136.31, 128.2 and 128.0 (aromatic ring); 104.15 and 96.83 (C-3, C-5).

Alternatively, title product of the preceding Example (6 g.) was stirred 16 hours, then refluxed for 4 hours and stripped to yield title product as a tacky foam, 6.2 g., which tlc (Rf and eluant as above) indicated of sufficient purity to be used directly in the next step.

In like manner, the same title product is prepared by solvolysis of the 2'-O-propionyl ester of the preceding Example.

EXAMPLE 7

4''-Epi-9-deoxo-9a-aza-9a-homoerythromycin A (VI)

Method A

Title product of Example 2 (40 g.) was dissolved 600 ml. $CH_3OH$. $NaBH_4$ (45 g.) was added over 45 minutes maintaining temperature less than 38°. The reaction mixture was stirred 64 hours, then stripped to a thick slurry containing excess borohydride and boron ester complex of product. The latter was distributed between 500 ml. each $CH_2Cl_2$ and $H_2O$, and the following sequence was repeated 3 times: The pH was adjusted with stirring to constant pH 2.5 with dilute HCl; the mixture was stirred vigorously 25 minutes; and the $H_2O$ layer was separated, combined with 500 ml. fresh $CH_2Cl_2$, adjusted to pH 9.5 with dilute NaOH and the $CH_2Cl_2$ layer separated. The pH 9.5 $CH_2Cl_2$ layer was combined with 500 ml. fresh $H_2O$ for repetition of the sequence On the third pass, the pH 9.5 $CH_2Cl_2$ layer was dried ($Na_2SO_4$) and stripped to yield crude title product as a foam, 34 g., which was crystallized from 150 ml. hot isopropyl ether, cooled and diluted with 300 ml. of pentane, affording purified title product, 25.8 g.; white crystals; tlc Rf 0.5 (9:1 $CHCl_3$:diethylamine); Rf 0.1 (90;10:1 $CH_2Cl_2$:$CH_3OH$:conc. $NH_4OH$), mp 170°–180°; $^1$Hnmr ($CDCl_3$) delta 2.26 [6H, s, $(CH_3)_2N$—], 3.29 (3H, s, cladinose $CH_3O$—); $^{13}$Cnmr [$CDCl_3$, $(CH_3)_4$ Si internal standard] ppm 179.44 (lactone C=O), 103.57 and 96.70 (C-3, C-5); 41.50 [$(CH_3)_2$—N—].

Method B

Unchromatographed title product of the preceding Example (6.2 g.) was dissolved in 200 ml. ethanol and hydrogenated over 12.5 g. Raney Ni at 50 psig for 18 hours. The reaction mixture was filtered, charged with 20 g. fresh Raney Ni and hydrogenation continued 4 hours. Filtration and fresh catalyst recharge were repeated, and hydrogenation continued for a further 16 hours. Filtration and stripping of the filtrate gave crude title product as a white foam. The latter was distributed between $CH_2Cl_2$ and saturated $NaHCO_3$, and the organic layer separated, dried ($Na_2SO_4$) and stripped to yield title product as a second white foam, 3.6 g., crystallized as above to yield purified title product, 955 mg., having physical properties identical with product prepared by Method A.

EXAMPLE 8

4″-Epi-9-deoxo-9a-hydroxy-9a-aza-9a-homoerythromycin A 3′-N-Oxide (X)

Stirring under $N_2$, title product of the preceding Example (3.0 g.) was dissolved in 15 ml. of 1:1 THF:$CH_3OH$. Thirty percent $H_2O_2$ (5 ml.) was added. After 0.5 hour, additional 30% $H_2O_2$ (2.5 ml.) was added. After a further 0.5 hour, the reaction mixture was cautiously poured into 1:1 $CH_2Cl_2$:$H_2O$ containing excess $Na_2SO_3$ (exothermic). The pH was 9. The aqueous layer was washed with fresh $CH_2Cl_2$ and then ethyl acetate. The organic layers were combined, dried ($Na_2SO_4$) and stripped to yield title product, 2.7 g., tlc Rf 0.15 (60:10:1 $CH_2Cl_2$:$CH_3OH$:conc. $NH_4OH$); $^1$Hnmr ($CDCl_3$)delta 3.21 [6H, s, $(CH_3)_2NO$], 3.38 (3H, s, cladinose $CH_3$—); MS: major peaks at m/e 576 (ion from desosamine fragmentation at C-5), 418 (N-hydroxyaglycone ion-minus both sugars). Both peaks diagnostic for —N—OH moiety with aglycone.

EXAMPLE 9

4″-Epi-9-deoxo-9a-methyl-9a-aza-9a-homoerythromycin A 3′-N-Oxide (XI)

Title product of the preceding Example (2.6 g., 0.0034 mole) was dissolved in 100 ml. $CH_2Cl_2$. With strong agitation, $K_2CO_3$ (37.5 g., 0.271 mole) and then $CH_3I$ (19.3 g., 8.5 ml. 0.136 mole) were added and the mixture stirred 20 hours. Filtration and stripping gave title product as a foam, 2.9 g.; tlc Rf 0.3 (60:10:1 $CH_2CH_2$:$CH_3OH$:conc. $NH_4OH$), Rf 0.15 (90:10:1 $CH_2Cl_2$:$CH_3OH$:conc. $NH_4OH$).

Title product prepared in this manner (2.8 g.) was further purified by chromatography on 85 g. silica gel using 90:10:1 $CH_2Cl_2$:$CH_3OH$:conc. $NH_4OH$ as eluant; thereby removing minor, more polar impurities. Recovery: 0.87 g; $^1$Hnmr ($CDCl_3$)delta 2.32

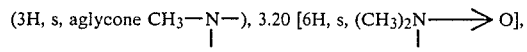, 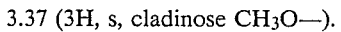

3.37 (3H, s, cladinose $CH_3O$—).

EXAMPLE 10

4″-Epi-9-deoxo-9a-methyl-9a-aza-9a-homoerythromycin A (IV)

Method A

Title product of Example 7 (0.706 g., 0.96 mmole) was dissolved in 20 ml. $CHCl_3$. Formaldehyde (37%, 0.078 ml.) and then formic acid (0.03 ml.) were added and the mixture stirred 4 hours, then refluxed 7 hours. The reaction mixture was cooled, added to 30 ml. $H_2O$ and adjusted to pH 9 with 6N NaOH. The organic layer was separated, dried ($Na_2SO_4$) and stripped to yield title product as a white foam, 0.7 g.; crystallized from hot ethanol/$H_2O$, 302 mg., mp 153°; recrystallized from hot ethanol/$H_2O$, 246 mg.; mp 155°; tlc Rf 0.55 (60:10:1 $CH_2Cl_2$:$CH_3OH$:conc. $NH_4OH$), Rf 0.6 (9:1 $CHCl_3$: diethylamine); $^1$Hnmr ($CDCl_3$)delta 2.29 [9H, broadened s, aglycone N—$CH_3$ desosamine $(CH_3)_2N$—], 3.31 (3H, s, cladinose $CH_3O$—); $^{13}$Cnmr ($CDCl_3$, $CDCl_3$ internal standard) ppm 178.89 (lactone C=O), 102.63 and 95.15 (C-3, C-5), 40.38 [$(C_3)_2N$—]; MS: major peaks at m/e 590 (N-methyl aglycone-desosamine ion via cladinose cleavage at C-1″), 416 [N-methyl aglycone ion (minus both sugars via cleavage at C-1″, C-5)], 158 (base peak, desosamine-derived fragment).

Method B

Unchromatographed title product of the preceding Example (0.242 g.) and 10% Pd/C (0.4 g.) were combined in 15 ml. 95% ethanol and the mixture hydrogenated at 50 psig for 1 hour. Catalyst was recovered by filtration and the filtrate evaporated to yield title product as a white foam, 160 mg., crystallized from ether/pentane, 124 mg., recrystallized from ethanol/$H_2O$, 95 mg., having physical properties identical with title product by Method A.

Method C

Chromatographically purified title product of the preceding Example (319 mg.) and Raney nickel (1.5 g., 50% water-wet) were combined in 20 ml. ethanol and hydrogenated at 50 psig for 1.5 hours. Catalyst was removed by filtration and the mother liquor evaporated to dryness to yield 205 mg. title product, identical in physical properties with title product by Method A.

EXAMPLE 11

2'-O-Acetyl-9-deoxo-9a-methyl-9a-aza-9a-homoerythromycin A

Title product of Preparation 5 (2.5 g., 3.34 mmoles) was stirred with acetic anhydride (0.339 ml., 3.60 mmoles) in 30 ml. $CH_2Cl_2$ for 4 hours. The reaction mixture was stripped and the residue dissolved in 50 ml. ethyl acetate, combined with 50 ml. $H_2O$ and the pH adjusted to 9.5 with 1N NaOH. The aqueous layer was separated and washed with 20 ml. fresh ethyl acetate. The organic layers were combined, dried ($NaSO_4$), stripped, dissolved in 30 ml. $CHCl_3$ and restripped to yield title product as a dry solid, 2.82 g., $^1$Hnmr/$CDCl_3$ includes delta 3.31 (C4"—$OCH_3$), 2.28 (N—$CH_3$), 2.25 [N—$(CH_3)_2$] and 2.0 (2'—$OCOCH_3$).

EXAMPLE 12

2'-O-Acetyl-4"-deoxy-4"-oxo-9-deoxo-9a-methyl-9a-aza-9a-homoerythromycin A (VIIIa)

Title product of the preceding Example (2.5 g., 3.2 mmoles) and DMSO (0.38 ml., 5.23 mmoles) were dissolved in 90 ml. $CH_2Cl_2$ and cooled to $-70°$ C. Maintaining a temperature less than $-50°$ C., trifluoroacetic anhydride (0.72 ml., 4.95 mmoles) was added by syringe and the mixture stirred 50 minutes at $-60°$. Triethylamine (1.54 ml., 11 mmoles) was added by syringe, maintaining less than $-50°$ during addition. The mixture was then warmed to $0°$, diluted with $H_2O$ and the pH adjusted to 9.5 with dilute NaOH. The organic layer was separated, dried ($NaSO_4$) to yield title product as a foam, 2.5 g. The foam was flash chromatographed on silica gel with 10:1 $CHCl_3$:$CH_3OH$ as eluant, monitoring by tlc and collecting 3 fractions. Cleanest product fraction 1, 1.7 g., was dissolved in $CHCl_3$, diluted with $H_2O$, adjusted to pH 4 with dilute HCl, and the aqueous layer separated, diluted with fresh $CHCl_3$, adjusted to pH 8 with dilute NaOH and the organic layer separated. The last aqueous layer was extracted with three portions of fresh $CHCl_3$. The last four organic layers were combined, backwashed with $H_2O$, dried ($Na_2SO_4$) and stripped to yield purified title product, 0.98 g.; tlc Rf 0.7 (5:1:0.1 $CHCl_3$ $CH_3OH$:$NH_4OH$); $^1$Hnmr ($CDCl_3$) includes delta (ppm): 2.05 (s, 3H, $COCH_3$), 2.26 [s, 6H, $N(CH_3)_2$], 2.33 (d, 3H, $NCH_3$) and 3.33 (d, 3H, $OCH_3$)

EXAMPLE 13

4"-Deoxy-4"-oxo-9-deoxo-9a-methyl-9a-aza-9a-homoerythromycin A (VIIa)

Title product of the preceding Example (0.93 g.) was dissolved in methanol. After 20 minutes the mixture was stripped to yield present title product, 0.74 g.; ms 746.4, 588.4, 573.4, 413.3, 158.1, 125.1; $^1$Hnmr ($CDCl_3$) includes delta (ppm): 5.5 (t, 1H, C1"—H), 4.6 (q, 1H, C5"—H), 3.35 (s, 3H, $OCH_3$), 2.38 (s, 3H, $NCH_3$), 2.30 [s, 6H, $N(CH_3)_2$].

EXAMPLE 14

4"-Epi-9-deoxo-9a-methyl-9a-aza-9a-homoerythromycin A (IV)

Title product of the preceding Example (0.25 g.) and 250 mg. of Raney nickel were combined in 20 ml. ethanol and hydrogenated under 50 psig for 4 hours. The catalyst was removed by filtration and the filtrate stripped to an oil which crystallized on standing. Title product was recovered by trituration with isopropyl ether and filtration, 0.13 g., identical in properties with the product of Example 10.

PREPARATION 1

4"-Epi-erythromycin A

A suspension of 100 g. of Raney nickel sludge in 1 liter of absolute ethanol containing 100 g of 4"-deoxy-4"-oxoerythromycin A (U.S. Pat. No. 4,510,220) was shaken in a hydrogen atmosphere overnight at room temperature at 50 psig. The spent catalyst was filtered over diatomaceous earth and the filtrate concentrated in vacuo to 300 ml. Water (700 ml.) was added to the concentrated filtrate and the resulting milky solution warmed on a steam bath. A small amount of ethanol was added to prevent gumming of the product as it precipitated from solution. After stirring for 2 hours at room temperature the product was filtered and dried, 57.6 g., and the filtrate concentrated in vacuo to the haze point. The mixture was allowed to stir for one hour and was filtered and dried, 21.4 g.

The resulting crops were combined, m.p. 141°–144° C. The $^1$Hnmr spectrum ($CDCl_3$) showed absorption at 3.3 (3H, s), 2.3 (6H, s) and 1.4 (3H, s) ppm.

PREPARATION 2

Erythromycin A Oxime Hydrochloride

Under $N_2$, erythromycin A (500 g., 0.681 mole) was dissolved in pyridine (2.787 Kg., 2.850 L, 35.29 mole). Hydroxylamine hydrochloride (1.183 Kg., 17.02 mole) was added and the mixture stirred for 22 hours, then stripped to a thick slurry and filtered with isopropanol wash. The combined filtrate and wash was restripped to a thick, waxy mass, which crystallized by trituration with 2 L of water, 615 g., (slightly water wet, used in the next step without thorough drying); tlc Rf 0.45 (60:10:1 $CH_2Cl_2$:$CH_3OH$:conc. $NH_4OH$).

By the same procedure, 5 g. of erythromycin A was converted to dried title product, 4.5 g., at least 95% pure by $^{13}$Cnmr. Recrystallization of 1 g. from 10 ml. methanol and 30 ml. isopropyl ether gave 725 mg.; mp 187° (dec.) [literature mp 188°–191°, Massey et al., Tetrahedron Letters, pp. 157–160, 1970]; $^{13}$Cnmr [DMSO-$d_6$, $(CH_3)_4$ Si internal standard] ppm 174.35 (lactone C=O), 168.78 (C=N—), 101.0 and 95.46 (C-3, C-5).

PREPARATION 3

9a-Aza-9a-homoerythromycin A

By the procedure of Example 2, with gas evolution noted on addition of the bicarbonate, slightly water wet, title product of the preceding Preparation (615 g., estimated to be 506 g., 0.613 mole on a dry basis was converted to crystalline title product, 416 g.; $^{13}$Cnmr [$CDCl_3$, $CDCl_3$ internal standard] ppm 177.54 (lactone C=O), 163.76 (amide C=O), 102.28 and 94.20 (C-3, C-5), 40.13 [$(CH_3)_2$N—].

PREPARATION 4

9-Deoxo-9a-aza-9a-homoerythromycin A

By reduction with $NaBH_4$ according to the method of Kobrehel et al. (supra), title product of the preceding preparation was converted to present title product.

PREPARATION 5

9-Deoxo-9a-methyl-9a-aza-9a-homoerythromycin A

By the procedure of Example 10 above, title product of the preceding Preparation (21.1 g., 0.0287 moles) was converted to present title product, initially isolated as a white foam, crystallized from hot ethanol/H₂O, 18.0 g., mp 136° C.

I claim:

1. 4''-Epi-9-deoxo-9a-methyl-9a-aza-9a-homoerythromycin A or a pharmaceutically-acceptable salt thereof.

2. A pharmaceutical composition which comprises an antibacterial amount of the compound of claim 1 and a pharmaceutically-acceptable carrier.

3. A method of treating a bacterial infection in a mammal which comprises administering to said mammal an antibacterially effective amount of the compound of claim 1.

4. A compound selected from the group consisting of 4''-epi-9a-aza-9a-homoerythromycin A and the 9-deoxo derivative thereof.

5. The compound of claim 4 which is 4''-epi-9a-aza-9a-homoerythromycin A.

6. The compound of claim 4 which is the 9-deoxo derivative of 4''-epi-9a-aza-9-homoerythromycin A.

7. 4''-Epi-erythromycin A oxime.

8. A compound selected from the group consisting of 9a-benzyloxycarbonyl-9-deoxo-4''-deoxy-4''-oxo-9a-aza-9a-homoerythromycin A and the 2'-O-(C2-C3)alkanoyl derivative thereof.

9. The compound of claim 8 which is 9a-benzyloxycarbonyl-9-deoxo-4''-deoxy-4''-oxo-9-aza-9a-homoerythromycin A.

10. The compound of claim 8 which is 2'-O-acetyl-9a-benzyloxycarbonyl-9-deoxo-4''-deoxy-4''-oxo-9-aza-9a-homoerythromycin A.

11. A compound selected from the group consisting of 2'-O-acetyl- and 2'-O-propionyl-9-deoxo-9a-benzyloxycarbonyl-9a-aza-9a-homoerythromycin A.

12. The compound of claim 11 which is 2'-O-acetyl-9-deoxo-9a-benzyloxycarbonyl-9a-aza-9a-homoerythromycin A.

13. A compound selected from the group consisting of 4''-epi-9-deoxo-9a-methyl-9a-aza-9a-homoerythromycin A 3'-N-oxide and 4''-epi-9-deoxo-9a-hydroxy-9a-aza-9a-homoerythromycin A 3'-N-oxide.

14. The 9a-hydroxy-3'-N-oxide of claim 13.

15. The 9a-methyl-3'-N-oxide of claim 13.

16. A compound selected from the group consisting of 4''-deoxy-4''-oxo-9-deoxo-9a-methyl-9a-aza-9a-homoerythromycin A and the 2'-O-(C₂–C₃)alkanoyl derivative thereof.

17. The compound of claim 16 which is 4''-deoxy-4''-oxo-9-deoxo-9a-methyl-9a-aza-9a-homoerythromycin A.

18. The compound of claim 16 which is 2'-O-acetyl-4''-deoxy-4''-oxo-9-deoxo-9a-methyl-9a-aza-9a-homoerythromycin A.

* * * * *